(12) United States Patent
Torii et al.

(10) Patent No.: US 8,721,078 B2
(45) Date of Patent: May 13, 2014

(54) FUNDUS PHOTOGRAPHING APPARATUS

(75) Inventors: Hisanari Torii, Gamagori (JP); Toshio Murata, Milpitas, CA (US)

(73) Assignee: Nidek Co., Ltd., Gamagori-Shi (JP)

( * ) Notice: Subject to any disclaimer, the term of this patent is extended or adjusted under 35 U.S.C. 154(b) by 89 days.

(21) Appl. No.: 13/307,669

(22) Filed: Nov. 30, 2011

(65) Prior Publication Data

US 2012/0140172 A1 Jun. 7, 2012

(30) Foreign Application Priority Data

Dec. 2, 2010 (JP) ................................. 2010-269822

(51) Int. Cl.
*A61B 3/14* (2006.01)
*A61B 3/10* (2006.01)
*A61B 3/12* (2006.01)

(52) U.S. Cl.
CPC ... *A61B 3/12* (2013.01); *A61B 3/14* (2013.01); *A61B 3/1225* (2013.01)
USPC .......................................... 351/206; 351/221

(58) Field of Classification Search
USPC .......... 351/205, 206, 221; 356/450, 451, 456, 356/477, 479; 382/131; 600/407, 425
See application file for complete search history.

(56) References Cited

U.S. PATENT DOCUMENTS

| 7,510,282 | B2 | 3/2009 | Ueno et al. | |
| 8,244,017 | B2 * | 8/2012 | Chun et al. | 382/131 |
| 2005/0084147 | A1 * | 4/2005 | Groszmann | 382/131 |
| 2010/0238403 | A1 * | 9/2010 | Kobayashi et al. | 351/206 |

FOREIGN PATENT DOCUMENTS

| JP | A-09-173298 | 7/1997 |
| JP | A-2008-029467 | 2/2008 |
| JP | A-2009-183332 | 8/2009 |

* cited by examiner

*Primary Examiner* — Mahidere Sahle
(74) *Attorney, Agent, or Firm* — Oliff PLC

(57) ABSTRACT

An ophthalmic photographing apparatus includes an optical coherence tomography device provided to imaging a tomographic image of an examinee's eye. The device includes: an irradiation position changing unit for changing an irradiation position of measurement light emitted from a light source on the eye to change an imaging position on the eye; and a detector for detecting a interference state between the measurement light reflected from the eye and reference light, and a displacement detecting unit provided to detect displacement in continuity between a tomographic image having already been obtained in a first imaging region and a tomographic image to be obtained in a second imaging region different from the first imaging region.

14 Claims, 4 Drawing Sheets

FUNDUS PHOTOGRAPHING APPARATUS

CROSS-REFERENCE TO RELATED APPLICATIONS

This application is based upon and claims the benefit of priority from the prior Japanese Patent Application No. 2010-269822, filed Dec. 2, 2010, the entire contents of which are incorporated herein by reference.

BACKGROUND

1. Technical Field

The present invention relates to an ophthalmic photographing or imaging apparatus for imaging a tomographic image of an eye by optical coherence tomography.

2. Related Art

An ophthalmic photographing apparatus including an optical coherence tomography (OCT) can obtain a tomographic image of an eye (e.g., a tomographic image of a fundus). The obtained tomographic image is used for evaluation of a condition of the eye (see Patent Document 1).

To obtain a panoramic image of a fundus, a fundus camera sequentially captures front images of an eye by moving a fixation target to thereby guide the eye to look at any of different target positions. The obtained front images are joined together to create the panoramic image (see Patent Document 2).

Further, in the OCT in Patent Document 3, a fixation target is moved to guide an eye to look at any of different target positions and three-dimensional tomographic images are sequentially imaged to obtain a panoramic image consisting of the three-dimensional tomographic images. Then, the obtained three-dimensional tomographic images are joined together to create the panoramic image.

In the case of obtaining a tomographic image of a peripheral part of an eye by use of the OCT, the eye is more likely to be unsteady as compared with imaging of a center part of the eye, and thus it is hard to image the peripheral part. The obtained tomographic image of the peripheral part with positional displacement or shift could not be joined smoothly with the tomographic image of the center part because of a difference in imaging position.

RELATED ART DOCUMENTS

Patent Documents

Patent Document 1: JP 2008-29467A (U.S. Pat. No. 7,510,282 B2)
Patent Document 2: JP9 (1997)-173298A
Patent Document 3: JP2009-183332A

SUMMARY

One object of the present invention to be achieved is to provide an ophthalmic photographing apparatus capable of appropriately imaging a panoramic tomographic image.

To achieve the above object, one aspect of the invention provides an ophthalmic photographing apparatus comprising: an optical coherence tomography device provided to imaging a tomographic image of an examinee's eye, the device including: an irradiation position changing unit for changing an irradiation position of measurement light emitted from a light source on the eye to change an imaging position on the eye; and a detector for detecting a interference state between the measurement light reflected from the eye and reference light, and a displacement detecting unit provided to detect displacement in continuity between a tomographic image having already been obtained in a first imaging region and a tomographic image to be obtained in a second imaging region different from the first imaging region.

BRIEF DESCRIPTION OF DRAWINGS

FIGS. 5A to 5I are diagrams showing overlapping regions of the imaging regions;

DETAILED DESCRIPTION

Figure 1:
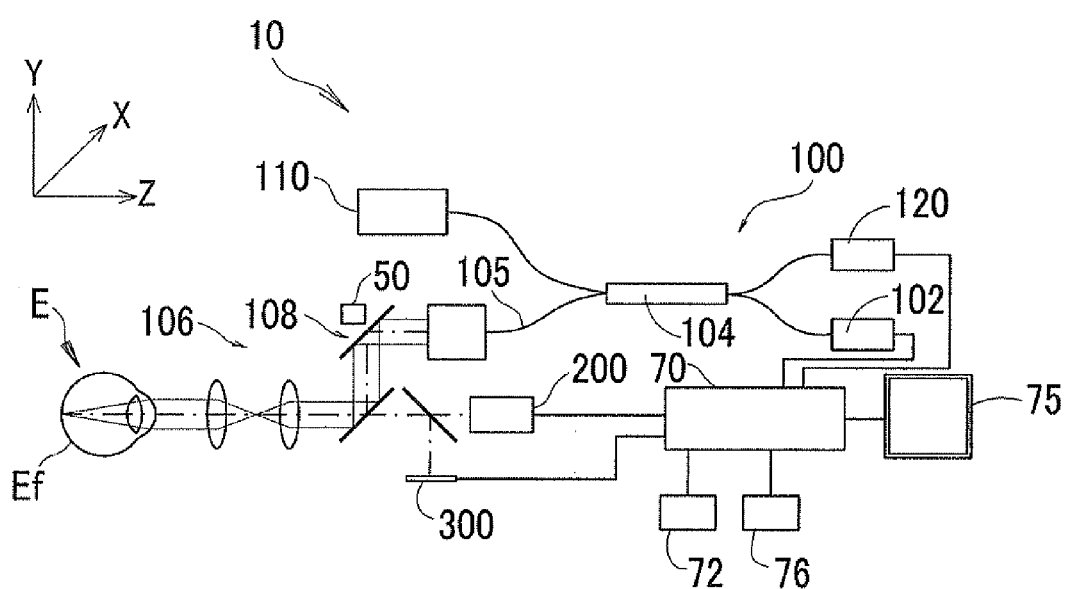
FIG. 1 is a diagram to schematically explain a configuration of an ophthalmic photographing apparatus in an embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The present embodiment will be explained below referring to the accompanying drawings. FIG. 1 is a diagram to schematically explain a configuration of an ophthalmic photographing (imaging) apparatus in the present embodiment. In this embodiment, an axial direction of an examinee's eye (an eye E) is referred to as a Z direction (right and left directions in FIG. 1), a horizontal direction is referred to as an X direction (an orthogonal direction to the drawing sheet of FIG. 1), and a vertical direction is referred to as a Y direction (up and down directions in FIG. 1). The surface direction of a fundus may also be referred to as a X-Y direction.

The configuration of the apparatus is schematically explained. This apparatus is an optical coherence tomography device (OCT device) 10 to capture a tomographic image of a fundus Ef of the examinee's eye E. The OCT device 10 includes an optical coherence system (OCT optical system) 100, a front observation optical system 200, a fixation target projecting unit 300, and a calculation and control unit (CPU) 70.

The OCT optical system 100 irradiates measurement light to the fundus Ef. This system 100 detects an interference state between the measurement light reflected from the fundus Ef and reference light by a light receiving element (a detector 120). The OCT optical system 100 includes an irradiation position changing unit (e.g., a optical scanner 108, the fixation target projecting unit 300) arranged to change an irradiation position of the measurement light on the fundus Ef in order to change an imaging position on the fundus Ef. The control unit 70 controls operations of the irradiation position changing unit based on set imaging position information and obtains a tomographic image based on a received signal from the detector 120.

<OCT Optical System>

The OCT optical system 100 is configured as a so-called ophthalmic optical tomography (OCT). The OCT optical system 100 splits the light emitted from a light source 102 into measurement light and reference light through a coupler 104. The OCT optical system 100 then delivers the measurement light to the fundus Ef of the eye E through a measurement optical system 106 and also delivers the reference light to a reference optical system 110. Thereafter, a detector (a light receiving element) 120 receives interference light which is a result of synthesis of the measurement light reflected by the fundus Ef and the reference light.

The detector 120 detects a interference state between the measurement light and the reference light. In the case of Fourier-domain OCT, a spectral intensity of the interference light is detected by the detector 120 and the spectral intensity data is subjected to Fourier transform so that a depth profile in a predetermined range is obtained. Other examples of the OCT are Spectral-domain OCT (SD-OCT), Swept-source OCT (SS-OCT), and Time-domain OCT (TD-OCT).

In the case of SD-OCT, a low-coherent light source (a broadband light source) is used as the light source 102. The detector 120 is provided with a spectral optical system (a spectrometer) configured to disperse the interference light into different frequency components (wavelength components). The spectrometer includes, for example, a diffracting grating and a line sensor.

In the case of SS-OCT, a wavelength scanning light source (a wavelength variable light source) configured to change an emission wavelength very fast is used as the light source 102, and a light receiving element alone, for example, is used as the detector 120. The light source 102 includes, for example, a light source, a fiber ring resonator, and a wavelength selectable filter. Examples of the wavelength selectable filter are a filter in which a diffracting grating and a polygonal mirror are combined, and a filter in which Fabry-Perot etalon is used.

The light emitted from the light source 102 is split into the measurement light beam and the reference light beam by the coupler 104. The reference light beam passes through the optical fiber 105 and then is emitted into atmosphere. This light beam is converged on the fundus Ef via the optical scanner 108, and other optical components of the measurement optical system 106. The light reflected by the fundus Ef travels a similar optical path and then returns to the optical fiber 105.

The optical scanner 108 scans the measurement light on the fundus Ef in the X-Y direction (a transverse direction). The optical scanner 108 is disposed at a position substantially conjugate with a pupil. For example, two galvano mirrors constitute the optical scanner 108, and reflection angles of the galvano mirrors are arbitrarily adjusted by a drive mechanism 50.

Accordingly, a reflecting angle (a traveling direction) of the light beam emitted from the light source 102 changes so that the scanning can be performed on the fundus Ef in any arbitrary direction. As a result, the imaging position on the fundus Ef is changed. Examples of the optical scanner 108 are reflection mirrors (galvano mirror, polygonal mirror, and resonant scanner), and an acousto-optic device (AOM) which changes a traveling direction of light (a deflection direction of light).

The reference optical system 110 generates the reference light to be synthesized with the measurement light reflected from the fundus Ef. The reference optical system 110 may be a Michelson optical system or a Mach-Zehnder optical system. The reference optical system 10 is for example constituted of a reflective optical system (e.g., a reference mirror). The light output from the coupler 104 is reflected by the reflective optical system to return to the coupler 104 so that the light is guided to the detector 120. Another example of the reference optical system 110 is a transmission optical system (for example, an optical fiber), wherein the light output from the coupler 104 is not returned thereto but is transmitted through the transmission optical system to be guided to the detector 120.

The reference optical system 110 is configured to move the optical members present in a reference optical path to change a difference in optical path length between the measurement light and the reference light. For example, the reference mirror is moved in the direction of an optical axis. A device for changing the difference in optical path length may be provided in a measurement optical path of the measurement optical system 106.

<Front Observation Optical System>

The front observation optical system 200 is provided to obtain a front image of the fundus Ef. This optical system 200 includes for example an optical scanner for scanning the measurement light (e.g., infrared light) emitted from a light source two-dimensionally on the fundus Ef and a second light receiving element for receiving the reflection light from the fundus Ef through a confocal opening placed at a position substantially conjugate with the fundus Ef. Thus, the optical system 200 is configured as a so-called ophthalmic scanning laser optometry (SLO).

As an alternative, the front observation optical system 200 may be configured as a fundus camera. The OCT optical system 100 can concurrently serve as an observation optical system 200, wherein the front image is captured based on the tomographic image data two-dimensionally obtained (for example, an integrated image of three-dimensional tomographic images in the depth direction, an integrated value of spectral data at each position in X and Y directions).

<Fixation Target Projecting Unit>

The fixation target projecting unit 300 includes an optical system for guiding a line of sight of the eye E. This projecting unit 300 has fixation targets to be presented to the eye E whereby to guide the eye E to in any of different directions.

For instance, the fixation target projecting unit 300 has a visible light source which emits visible light and is arranged to change the target presenting position two-dimensionally, thereby changing the sight line direction so that a site to be imaged (an imaging site) is changed. For example, when a fixation target is presented in the same direction as the imaging optical axis, a center part of the fundus Ef is set as the imaging site. Further, when the fixation is presented above the imaging optical axis, an upper part of the fundus Ef is set as the imaging site. That is, the imaging site is changed according to the position of the target with respect to the imaging optical axis.

For example, the fixation target projecting unit 300 is configured to adjust the fixation position by using LED lighting positions arranged in a matrix shape or adjust the fixation position by scanning the light from the light source using the optical scanner for lighting control of the light source. The projecting unit 300 may be an internal fixation lamp or an external fixation lamp.

<Control Part>

The control unit 70 controls the entire apparatus such as components of each configuration 100 to 300. The control unit 70 shares an image processor for processing an obtained image, an image analyzer for analyzing the obtained image, and others. The control unit 70 is realized by a general CPU (Central Processing Unit) or the like.

Figure 2A:
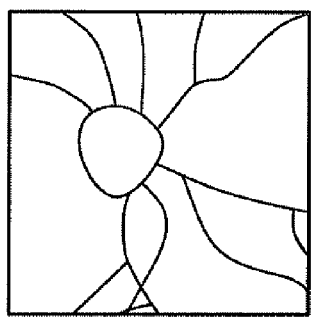
FIG. 2A shows an example of a front image obtained through a front observation optical system.
Figure 2B:
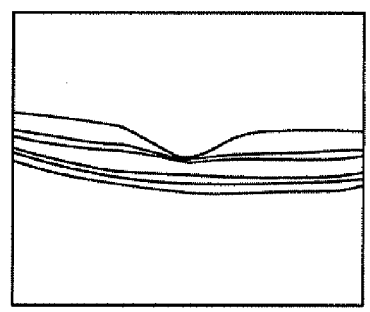
FIG. 2B shows an example of a tomographic image obtained through an OCT optical system.

FIG. 2A shows an example of a front image obtained by the front observation optical system 200 and FIG. 2B shows an example of a tomographic image obtained by the OCT optical system 100. For instance, the control unit 70 acquires a tomographic image (an OCT image) by image processing based on a light received signal output from the detector 120 of the OCT optical system 100 and also obtains a front image based on a light received signal output from a light receiving element of the front observation optical system 200. The control unit 70 controls the fixation target projecting unit 300 to change a fixation position.

A memory (a storage part) 72, a monitor 75, a mouse (an operation input part) 76 are respectively electrically connected to the control unit 70. The control unit 70 controls a display screen of the monitor 75. An obtained fundus image is output as a still image or moving image on the monitor 75 and also stored in the memory 72. The memory 72 records e.g. imaged tomographic images, front images, various information related to imaging such as information on an imaging position of each tomographic image, etc. The control unit 70 controls each component of the OCT optical system 100, the front observation optical system 200, and the fixation target projecting unit 300 based on an operation signal output from the mouse 76. For the details of the configuration of the above OCT device 10, refer to JP 2008-29467A for example.

<Explanation of Operations>

Figure 3A:
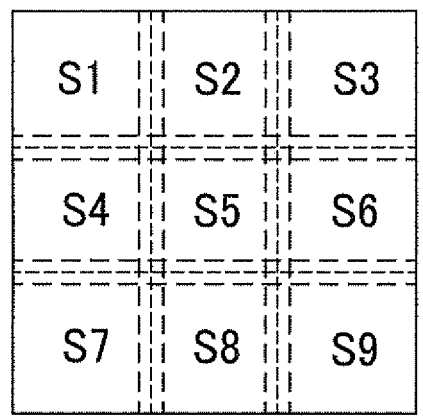
FIG. 3A is a diagram showing an example of a plurality of imaging regions set to obtain a panoramic three-dimensional tomographic image.
Figure 3B:
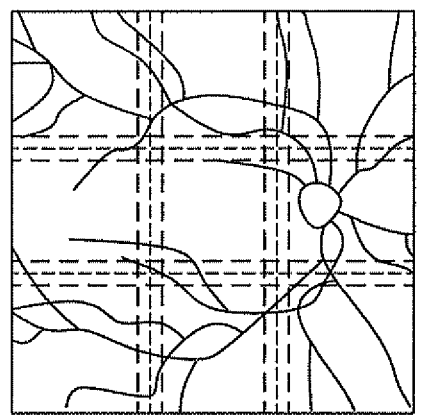
FIG. 3B is a diagram showing a relationship between each imaging region and a fundus.
Figure 4:
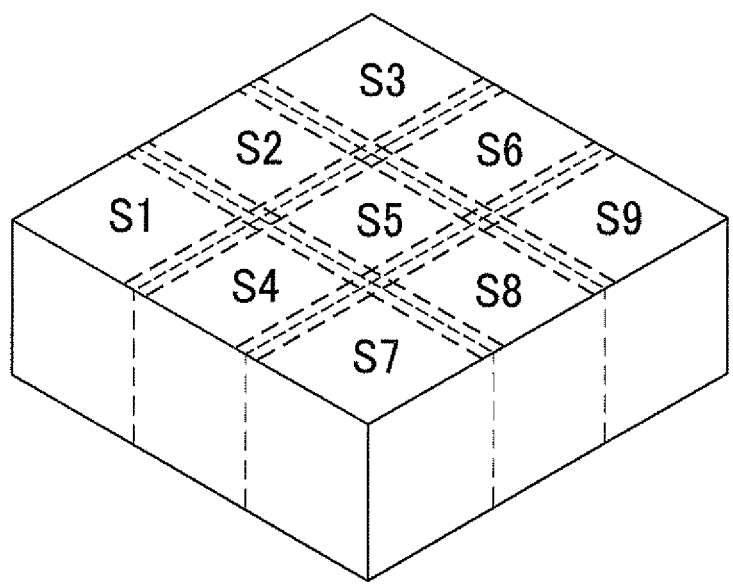
FIG. 4 is a view to stereoscopically explain each imaging region in FIG. 3A.

FIG. 3A shows an example of imaging regions set to obtain a panoramic image from three-dimensional tomographic images. FIG. 3B shows a relationship between each imaging region in FIG. 3A and a fundus. FIG. 4 is a diagram to stereoscopically show the imaging regions. FIGS. 5A to 5I are diagrams showing overlapping regions of the imaging regions.

In the present embodiment, the control unit 70 sets a plurality of imaging regions (e.g., nine imaging regions S1 to S9) on the fundus Ef in order to obtain a panoramic tomographic image consisting of a plurality of three-dimensional tomographic images. The imaging regions are different in tomographic image imaging position on the fundus Ef. Two adjacent imaging regions partly overlap each other (see small band portions defined by broken lines in FIGS. 3A, 3B, and 5A to 5I). Those imaging regions may be set arbitrarily or set in advance.

The control unit 70 controls the projecting unit 300 to present a target at a position corresponding to each imaging region. The control unit 70 obtains a panoramic image from the tomographic image obtained in each imaging region.

When the imaging region is to be changed, for example, the control unit 70 sequentially changes the target position in the previously set order. The imaging region also may be changed arbitrarily based on an operation signal from the mouse 76.

When the target is presented at a certain position, the control unit 70 controls the OCT optical system 100 to capture a three-dimensional tomographic image corresponding to each set region and also controls the observation optical system 200 to obtain a front image.

To obtain the three-dimensional tomographic image, the control unit 70 controls the operation of the optical scanner 108 to make two-dimensional scan of the measurement light in the X-Y directions in a scanning area corresponding to the imaging region, thereby obtaining a three-dimensional tomographic image. Please note that a scanning pattern may include a raster scan pattern and a multiple-line scan pattern.

The captured tomographic image and front image are displayed as an observation image in the form of a moving image on the monitor 75. The obtained tomographic image and front image are associated with the imaging region and stored as a still image in the memory 72. Obtaining the front image may be conducted at the same time as obtaining the tomographic image or before or after obtaining the tomographic image.

<OCT Tracking Using Previously Obtained Image>

The control unit 70 detects displacement or shift in continuity between a tomographic image previously obtained in a first imaging region and a tomographic image to be obtained in a second imaging region different from the first imaging region. The control unit 70 compensates an irradiation position of the measurement light relative to the fundus Ef based on a detection result thereon.

For instance, the control unit 70 detects displacement in continuity of images in consideration of changes in sight line between a target position in the first imaging region and a target position in the second imaging region. To detect the displacement, the control unit 70 acquires a front image of the eye including a tomographic image imaging position.

Assuming that a first front image corresponding to the first imaging region is a reference image, the control unit 70 performs matching of a second front image obtained in the second imaging region with the first front image by utilizing the overlapping portions of the first front image and the second front image. The control unit 70 then detects displacement in continuity based on a result of the matching. Herein, the control unit 70 detects displacement between the first front image and the second front image in a surface direction (X-Y directions) of the fundus Ef.

One example of detecting displacement in continuity of images is explained below. For instance, a front image already obtained in a previous imaging region is used for tracking to obtain a three-dimensional tomographic image in a subsequent imaging region. For example, the control unit 70 performs compensation processing to the front image already obtained in the previous imaging region, according to the movement of the sight line of the eye E. The control unit 70 sets this image as a reference image and detects a relative position to a front image to be obtained in the subsequent imaging region. The control unit 70 compensates the OCT scanning position based on a detection result so as to measure a desired region of the fundus Ef even when the eye E moves.

A case of sequentially obtaining tomographic images in adjacent two imaging regions (e.g., an imaging region S3 and an imaging region S6) is explained below. In the following explanation, the imaging region S6 denotes a first imaging region and the imaging region S3 denotes a second imaging region. A first three-dimensional tomographic image and a first front image represent a three-dimensional tomographic image and a front image obtained at a fixation position corresponding to the first imaging region S6. A second three-dimensional tomographic image and a second front image represent a three-dimensional tomographic image and a front image obtained at a fixation position corresponding to the second imaging region S3.

Firstly, the control unit 70 presents a target corresponding to the first imaging region S6 and obtains a first three-dimensional tomographic image and a first front image corresponding thereto. Secondly, the control unit 70 switches the target presenting position to a position corresponding to the second imaging region S3 in order to obtain a second three-dimensional tomographic image.

Figure 6A:
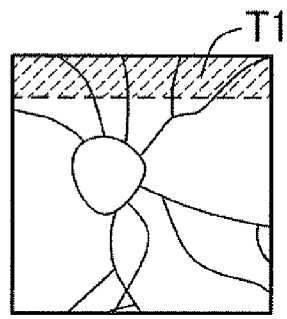
FIG. 6A shows an example of a first front image.
Figure 6B:
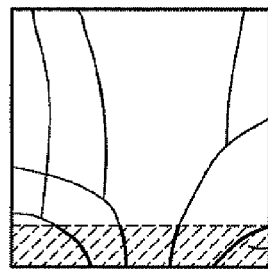
FIG. 6B shows an example of a second front image.

FIG. 6A shows an example of the first front image and FIG. 6B shows an example of the second front image. It is necessary to consider in detecting a relative position between the first front image and the second front image that those first and second front images are different in imaging region and the sight line of the eye E changes.

For instance, to obtain a reference image for tracking, the control unit 70 extracts a portion (an overlapping portion T1) of the first front image in which the imaging region overlaps with the second front image (see FIG. 6A). Herein, a deflection angle of the eye E is well known. Thus, a coordinate position of the overlapping portion of each front image is determined in advance by simulation, experiment, or the like. Other portions than the overlapping portion T1 are trimmed.

On the other hand, a portion of the second front image (an overlapping portion T2) in which its imaging region overlaps with the first front image appears on the side adjacent to the first imaging region (see FIG. 6B). In other words, the overlapping portion T1 and the overlapping portion T2 appear symmetrically relative to the center of an imaging region. If the eye does not move, the relative positions of the overlapping portion T1 and the overlapping portion T2 depend on a change amount of the sight line direction of the eye E guided by the projecting unit 300.

Figure 7A:
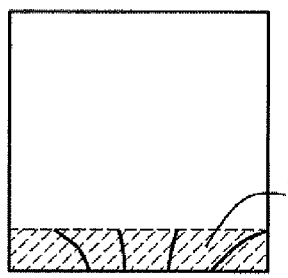
FIG. 7A shows a first front image after an overlapping portion has been moved.

Therefore, the control unit 70 virtually moves an image corresponding to the overlapping portion T1 by image processing based on the change amount of the sight line direction (FIG. 7A shows a first front image with the overlapping portion T1 having been moved). The control unit 70 stores this image of the moved overlapping portion T1 as a reference image for tracking in the memory 72. Specifically, the image corresponding to the overlapping portion T1 is moved from an upper end to a lower end in the imaging region of the front image.

When the target position is changed, the control unit 70 starts tracking using the first front image stored as the reference image in the memory 72. The control unit 70 continually obtains the second front image through the observation optical system 200. The control unit 70 performs template matching (evaluation by cross-correlation analysis between the reference image and the measured image) with respect to the second front image by use of the aforementioned reference image to detect the reference image in the second front image.

Figure 7B:
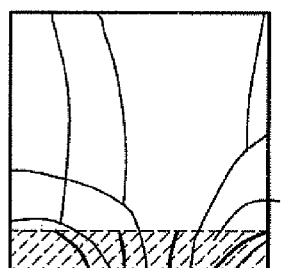
FIG. 7B is a diagram to explain a relationship of overlapping portions with positional displacement.

If there is no positional displacement, the reference image is detected at the same position as the first front image (see FIG. 6B). If there is positional displacement, on the other hand, the reference image is detected in a deviated position from the position of the first front image according to a displacement direction and a displacement amount (see FIG. 7B). The control unit 70 then detects displacement or deviation of a scanning position based on the detected coordinate position.

For instance, the control unit 70 moves the reference image on the second front image, horizontally/vertically/rotationally, to detect a site at which a correlation value is maximum. The control unit 70 obtains, as a central coordinate position, a site at which the correlation value is maximum in the reference image. Thereafter, the control unit 70 calculates movement information of the central coordinate position (e.g., a moving direction, a moving amount) between the reference image and the second front image. A calculated value denotes positional displacement information ΔP.

<Setting Subsequent Scanning Position>

The control unit 70 controls the OCT optical system 100 to obtain a second three-dimensional tomographic image based on a trigger signal. Specifically, the control unit 70 compensates the scanning position of the measurement light based on a positional displacement detection signal (positional displacement information ΔP). When two-dimensional scanning is to be performed in the X-Y directions, preferably, the control unit 70 compensates the scanning position in each line scan. For instance, the control unit 70 adds the positional displacement information ΔP to each of a scanning start point and a scanning end point both set in advance, thereby setting compensated positions. Needless to say, the scanning position may be compensated in units of plural scanning lines or compensated in the entire scanning range.

When the three-dimensional tomographic image in the second imaging region S3 is obtained as above, the control unit 70 controls the projecting unit 300 to project a target at a position corresponding to a next imaging region. The control unit 70 then controls the OCT optical system 100 to capture a three-dimensional tomographic image in the next imaging region. In this way, the control unit 70 sequentially obtains each three-dimensional tomographic image to create a panoramic image from the three-dimensional tomographic images and stores those three-dimensional tomographic images in the memory 75.

Figures 5A, 5B, 5C, 5D, 5E, 5F, 5G, 5H, 5I:
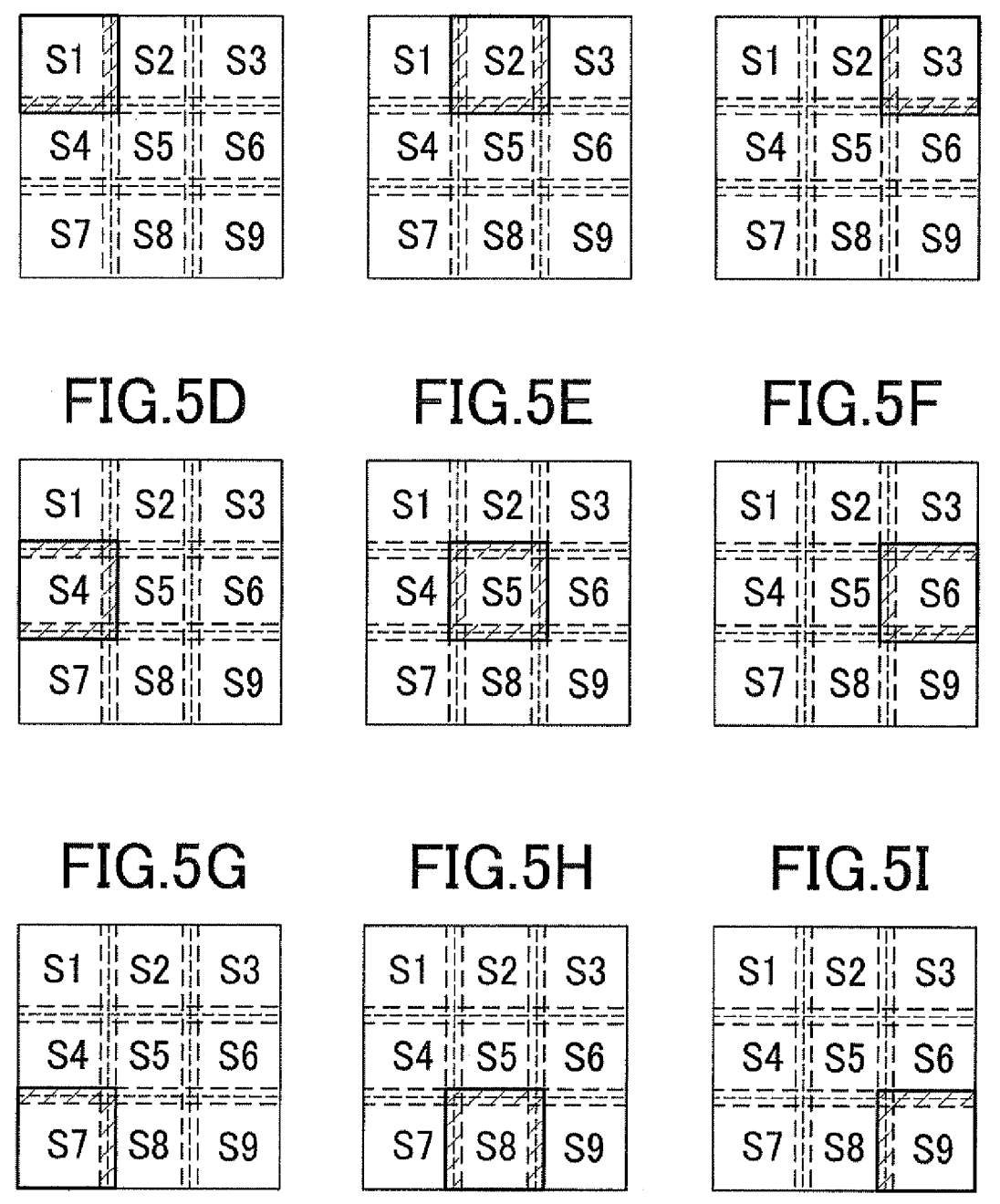

For instance, as shown in FIG. 5E, in the case of obtaining a three-dimensional tomographic image in the imaging region S5, a left side portion of the front image corresponding to the imaging region S6 and a right side portion of the front image corresponding to the imaging region S5 overlap each other in relation to the imaging regions. Further, as shown in FIG. 5I, in the case of obtaining a three-dimensional tomographic image in the imaging region S9, an upper side portion of the front image corresponding to the imaging region S9 and a lower side portion of the front image corresponding to the imaging region S6 overlaps each other in relation to the imaging regions. Accordingly, the positional displacement is detected by use of those overlapping portions and tracking is conducted between different imaging regions.

Naturally, the reference image for tracking is not limited to the front image in the imaging region S6. For instance, in the case of obtaining a tomographic image corresponding to the imaging region S1, at least one of the imaging regions S2, S4, and S5 is used as a front image of an adjacent imaging region to the imaging region S1. In this case, a synthesized image of a plurality of front images may be used as a reference image.

It is to be noted that an image including many characteristic points (e.g., a blood vessel) is preferably chosen as the reference image. Further, an image obtained at a center fixation target position providing stable fixation may also be used as the reference image. The order of imaging the imaging regions is not limited to any particular order, but it is preferable to obtain first an image having many characteristic points (e.g., a blood vessel). Further, an image at the center fixation position may be obtained first.

When the three-dimensional tomographic images in respective imaging regions are obtained as above, the control unit 70 joins the image data of each image stored in the memory 72 by image processing to create a panoramic three-dimensional tomographic image. The panoramic OCT image obtained as above includes fundus tomographic information of an examinee's eye in a wide range and hence is utilized for early detection of abnormalities of an eye or the like.

For instance, the control unit 70 measures a thickness distribution of retinal layers in the panoramic tomographic image by image processing. The control unit 70 then compares the layer thickness distribution stored in a data base for a normal eye and the layer thickness distribution of the eye E to determine whether the eye E is normal or not. Accordingly, an analysis result is obtained based on the layer thickness distribution over a wider range of the fundus Ef. This contributes to easy detection of abnormalities of the eye.

In such a case, tracking is performed using the front image previously obtained as above, so that each three-dimensional tomographic image constituting the panoramic image is obtained at an exact imaging position, and a good panoramic image can be created. Consequently, it is easy to detect an affected part and detection accuracy of the affected part can be enhanced.

When the panoramic tomographic image is to be created after each tomographic image is obtained, the control unit 70 may make positioning between the three-dimensional tomographic images so that respective characteristic points (e.g., a blood vessel) of the tomographic images are smoothly continuous with each other. For instance, positioning is performed by image processing using a blood vessel portion included in each three-dimensional tomographic image. By this manner, displacement of imaging positions can be further canceled by a combination of tracking during image acquisition and positioning after image acquisition. For positioning them, it may utilize an OCT fundus image (e.g., an integrated image) formed from a three-dimensional tomographic image or a front image corresponding to each three-dimensional tomographic image may be utilized.

Furthermore, the control unit 70 may be arranged to relatively rotate a first three-dimensional tomographic image obtained in the first imaging region and a second three-dimensional tomographic image obtained in the second imaging region to thereby compensate displacement between those three-dimensional tomographic images.

For instance, the control unit 70 compensates displacement by image processing to smoothly join the layers included in the three-dimensional images of the retina with each other. For example, the control unit 70 has only to perform image processing of rotating the second three-dimensional tomographic image about a roll axis, a pitch axis, and a yawing axis with respect to the first three-dimensional tomographic image.

In the above embodiment, the front image used for tracking may be an unprocessed (raw) image obtained through the observation optical system 200 or a processed image subjected to certain image processing (e.g., vessel blood extracting processing). Further, the image used for tracking is not limited to a front image as long as it is a schematic or rough image whereby the fundus is identified. For example, a tomographic image is used as the schematic image. At that time, a characteristic point (e.g., papilla, macula, affected part, each layer of retina, etc.) in the three-dimensional tomographic image may be utilized.

Further, a first schematic image and a second schematic image may also be different in kind (e.g., a front image before image processing and a front image after image processing). Moreover, the first schematic image and the second schematic image may also be obtained through different optical systems (e.g., the first schematic image is a front image obtained from data forming a three-dimensional tomographic image and the second schematic image is a front image obtained through the SLO optical system).

In the aforementioned embodiment, when a relative position between the first front image and the second front image is to be detected in consideration of a change amount in the sight line direction, the control unit 70 does not need to move the overlapping portion T1. For instance, the control unit 70 retrieves an imaging region corresponding to the overlapping portion T1 in the second front image and then detects a coordinate position of the imaging region corresponding to the overlapping portion T1. The control unit 70 then offsets the detected coordinate position according to the change of the sight line direction. Thus, the relative position determined by taking account the sight line direction is detected.

In the above embodiment, the target position is changed by the projecting unit 300, thereby changing the imaging region. In this case, any configurations may be adopted as long as the irradiation position of the measurement light on the fundus Ef can be changed. For instance, the control unit 70 may change the traveling direction of a measurement beam by the optical scanner 108 to change the imaging region. The optical scanner 108 and the projecting unit 300 may also be utilized in combination.

In the above embodiment, an imaging range of the three-dimensional tomographic image obtained through the OCT optical system 100 and an imaging range of the front image obtained through the observation optical system 200 may be equal in size or different in size.

The above embodiment exemplifies obtaining a panoramic three-dimensional tomographic image but is not limited thereto. The control unit 70 obtains OCT tomographic images in different imaging regions and then obtains a panoramic OCT tomographic image based on the obtained OCT tomographic images. For instance, the control unit 70 obtains a panoramic tomographic image in a certain transverse direction.

Figure 8A:
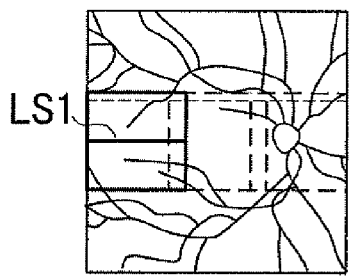
FIGS. 8A to 8C are diagrams showing concrete examples to obtain a panoramic image by line scan.
Figure 8B:
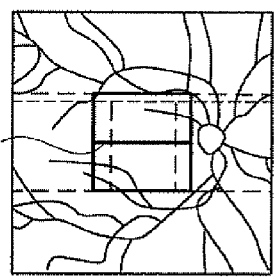
Figure 8C:
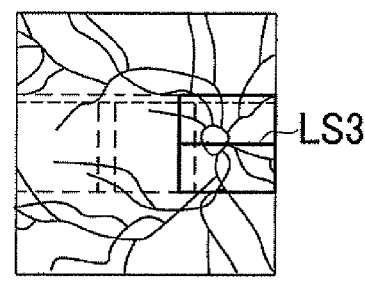

FIGS. 8A, 8B, and 8C show concrete examples to obtain a panoramic image by line scan. In the figures, LS1, LS2, and LS3 denote scan lines. For instance, the control unit 70 obtains a line scan image covering over a wide range of the fundus Ef and therefore line scan (LS1, LS2, LS3) is performed in different imaging regions so that end portions of the adjacent tomographic images are continuous with each other. Even in this case, the control unit 70 obtains front images corresponding to each tomographic image. When a tomographic image of a next imaging region is to be obtained, the control unit 70 performs tracking by use of a previously obtained front image. The tomographic images obtained by scan lines are joined to create a panoramic image.

In the above embodiment, the control unit 70 compensates the measurement position by use of a displacement detection result. It is to be noted that the control unit 70 may cause the monitor 75 to display the displacement detection result (e.g., to electronically display a displacement direction and a displacement amount). In this case, the examiner is allowed to adjust the measurement position by hand while watching the monitor 75. The displacement information helps to determine the timing of obtaining a tomographic image.

The above embodiment shows an example of the apparatus for obtaining a tomographic image of a fundus. The aforementioned method of obtaining a panoramic tomographic image is applied to an apparatus for obtaining a tomographic image of an eye. For example, it is also applicable to an apparatus for obtaining a tomographic image of an anterior segment of an eye. For the anterior segment, for example, an optical system for observing the front of an anterior segment and the front image of the anterior segment is used as a schematic image for detecting positional displacement between imaging regions.

A method of detecting positional displacement between two images may be selected from various image processing methods (a method using various correlation functions, a method using a Fourier transform, a method based on matching of characteristic points).

For instance, a conceivable method is achieved by displacing a reference image or a measured image (a current fundus image) by one pixel, comparing the reference image with a target image, and detecting a positional displacement direction and a positional displacement amount between the reference image and the target image when they coincide most closely with each other (when the correlation is highest). Another conceivable method is achieved by extracting common characteristic points from a predetermined reference image and a target image and detecting a positional displacement direction and a positional displacement amount of the extracted characteristic point.

An evaluation function in template matching may be based on SSD (Sum of Squared Difference) representing the similarities, SAD (Sum of Absolute Difference) representing the differences, or the like.

The foregoing detailed description has been presented for the purposes of illustration and description. b Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

The invention claimed is:

1. An ophthalmic photographing apparatus comprising:
an optical coherence tomography device provided to imaging a tomographic image of an examinee's eye, the device including:
an irradiation position changing unit for changing an irradiation position of measurement light emitted from a light source on the eye so that the irradiation position is changed in a surface direction of a fundus of the eye to change an imaging position on the eye at least between a first imaging region and a second imaging region different from the first imaging region in the surface direction of the fundus; and
a detector for detecting an interference state between the measurement light reflected from the eye and reference light, and
a displacement detecting unit provided to detect displacement in continuity in the surface direction of the fundus between a tomographic image having already been obtained in the first imaging region and a tomographic image to be obtained in the second imaging region changed by the irradiation position changing unit and different from the first imaging region in the surface direction of the fundus.

2. The ophthalmic photographing apparatus according to claim 1, further including a compensating unit for compensating a relative irradiation position of the measurement light in the surface direction of the fundus with respect to the eye based on a detection result of the displacement detecting unit.

3. The ophthalmic photographing apparatus according to claim 2, wherein
the optical coherence tomography device includes an optical scanner to scan the measurement light on the examinee's eye, and
the compensating unit controls operation of the optical scanner based on the detection result of the displacement detecting unit to compensate a scanning position of the measurement light with respect to the eye.

4. The ophthalmic photographing apparatus according to claim 1, wherein
the optical coherence tomography device is an optical coherence tomography device for imaging a tomographic image of a fundus, the device including:
a fixation target projecting unit having a fixation target and being configured to guide the examinee's eye in a plurality of directions; and
a controller configured to control the fixation target projecting unit to present a target at a position corresponding to each of the imaging regions.

5. The ophthalmic photographing apparatus according to claim 4, further including an image processor for obtaining a panoramic mage of the tomographic images obtained respectively in the imaging regions.

6. The ophthalmic photographing apparatus according to claim 4, wherein
the optical coherence tomography device includes an optical scanner for scanning the measurement light on the fundus, and
the controller controls operation of the optical scanner to scan the measurement light two-dimensionally on the fundus and obtain a three-dimensional tomographic image in each of the imaging regions.

7. The ophthalmic photographing apparatus according to claim 4, wherein
the displacement detecting unit detects displacement in continuity in consideration of a change in a sight line direction of the examinee's eye between a target position in the first imaging region and a target position in the second imaging region.

8. The ophthalmic photographing apparatus according to claim 4, wherein
the displacement detecting unit includes an optical system for obtaining reflection light from the examinee's eye to obtain a schematic image of the eye including a tomographic image imaging position, and
the displacement detecting unit is arranged to perform matching between a first schematic image corresponding to the first imaging region and being assumed as a reference image and a second schematic image obtained in the second imaging region by utilizing overlapping portions of the first and second schematic images, and detect the displacement in continuity based on a result of the matching.

9. The ophthalmic photographing apparatus according to claim 8, wherein
the displacement detecting unit detects displacement in a surface direction of the fundus between a first schematic image and a second schematic image as the displacement in continuity.

10. The ophthalmic photographing apparatus according to claim 6, further including an image processor configured to perform image processing of relatively rotating a first three-dimensional tomographic image obtained in the first imaging region and a second three-dimensional tomographic image obtained in the second imaging region to compensate displacement between the three-dimensional tomographic images.

11. The ophthalmic photographing apparatus according to claim 1, wherein the irradiation position changing unit includes at least one of a fixation target projecting unit having a fixation target and being configured to guide the examinee's eye in a plurality of directions, and an optical scanner for scanning the measurement light on the eye.

12. An ophthalmic photographing apparatus comprising:
an optical coherence tomography device provided to imaging a tomographic image of an examinee's eye, the device including:
an irradiation position changing unit for changing an irradiation position of measurement light emitted from a light source on the eye to change an imaging position on the eye; and
a detector for detecting an interference state between the measurement light reflected from the eye and reference light, and
a displacement detecting unit provided to detect displacement in continuity between a tomographic image having already been obtained in a first imaging region and a tomographic image to be obtained in a second imaging region different from the first imaging region,
wherein the optical coherence tomography device is an optical coherence tomography device for imaging a tomographic image of a fundus, the device including:
a fixation target projecting unit having a fixation target and being configured to guide the examinee's eye in a plurality of directions; and
a controller configured to control the fixation target projecting unit to present a target at a position corresponding to each of the imaging regions,
the displacement detecting unit includes an optical system for obtaining reflection light from the examinee's eye to obtain a schematic image of the eye including a tomographic image imaging position, and
the displacement detecting unit is arranged to perform matching between a first schematic image corresponding to the first image region and being assumed as a reference image and a second schematic image obtained in the second imaging region by utilizing overlapping portions of the first and second schematic images, and detect the displacement in continuity based on a result of the matching.

13. The ophthalmic photographing apparatus according to claim 12, wherein the displacement detecting unit detects displacement in a surface direction of the fundus between a first schematic image and a second schematic image as the displacement in continuity.

14. An ophthalmic photographing apparatus comprising:
an optical coherence tomography device provided to imaging a tomographic image of an examinee's eye, the device including:
an irradiation position changing unit for changing an irradiation position of measurement light emitted from a light source on the eye to change an imaging position on the eye; and
a detector for detecting an interference state between the measurement light reflected from the eye and reference light, and
a displacement detecting unit provided to detect displacement in continuity between a tomographic image having already been obtained in a first imaging region and a tomographic image to be obtained in a second imaging region different from the first imaging region,
wherein the displacement detecting unit includes an optical system for obtaining reflection light from the examinee's eye to obtain a schematic image of the eye including a tomographic image imaging position, and
the displacement detecting unit is arranged to perform matching between a first schematic image corresponding to the first imaging region and being assumed as a reference image and a second schematic image obtained in the second imaging region by utilizing overlapping portions of the first and second schematic images, and detect the displacement in continuity based on a result of the matching.

\* \* \* \* \*